United States Patent [19]
Gerner et al.

[11] Patent Number: 5,885,332
[45] Date of Patent: Mar. 23, 1999

[54] SOLVENT RECEPTACLE AND DEGASSER FOR USE IN HIGH PRESSURE LIQUID CHROMATOGRAPHY

[76] Inventors: Yuri Gerner, 2086 Timmy St., Mendota Heights, Minn. 55120; Carl W. Sims, 1136 Colette Pl., St. Paul, Minn. 55116

[21] Appl. No.: 900,055

[22] Filed: Jul. 24, 1997

Related U.S. Application Data

[63] Continuation-in-part of Ser. No. 688,439, Jan. 30, 1996, Pat. No. 5,743,941, which is a continuation-in-part of Ser. No. 468,016, Jun. 6, 1995, abandoned.

[51] Int. Cl.[6] .................................................. B01D 53/22
[52] U.S. Cl. ............................ 96/10; 96/12; 96/106; 96/194; 55/355
[58] Field of Search .................... 55/355; 95/46, 95/248, 266; 96/6, 10, 11, 12, 101, 106, 193, 194; 210/188

[56] References Cited

U.S. PATENT DOCUMENTS

| | | | |
|---|---|---|---|
| 3,184,358 | 5/1965 | Utz | 156/126 |
| 3,734,139 | 5/1973 | Zafiroglu | 138/146 |
| 3,751,880 | 8/1973 | Holm . | |
| 3,946,905 | 3/1976 | Cogliano | 222/107 |
| 3,972,695 | 8/1976 | Buckley et al. | 96/10 |
| 4,196,464 | 4/1980 | Russell | 361/215 |
| 4,243,074 | 1/1981 | Strutzel et al. | 138/118.1 |
| 4,469,495 | 9/1984 | Hiraizumi et al. . | |
| 4,523,934 | 6/1985 | Joshua | 55/307 |
| 4,791,965 | 12/1988 | Wynn | 138/146 |
| 4,801,501 | 1/1989 | Harlow | 428/383 |
| 4,915,713 | 4/1990 | Buzza et al. | 95/266 |
| 4,925,710 | 5/1990 | Buck et al. | 428/34.5 |
| 4,950,315 | 8/1990 | Gollan | 55/356 |
| 5,167,259 | 12/1992 | Brunnhofer | 138/137 |
| 5,183,486 | 2/1993 | Gatten et al. | 96/193 |
| 5,234,663 | 8/1993 | Jones et al. | 422/46 |
| 5,261,937 | 11/1993 | Jiang et al. | 96/101 |
| 5,279,647 | 1/1994 | Gatten et al. | 96/193 |
| 5,284,184 | 2/1994 | Noone et al. | 138/121 |
| 5,290,340 | 3/1994 | Gatten et al. | 95/46 |
| 5,298,225 | 3/1994 | Higdon | 422/89 |
| 5,313,987 | 5/1994 | Rober et al. | 138/137 |
| 5,340,384 | 8/1994 | Sims | 96/6 |
| 5,341,849 | 8/1994 | Mang | 138/133 |
| 5,365,938 | 11/1994 | Eskela | 128/719 |
| 5,425,803 | 6/1995 | VanSchravendijk et al. | 95/46 |
| 5,437,311 | 8/1995 | Reynolds | 138/115 |
| 5,607,581 | 3/1997 | Gerner et al. | 96/101 |
| 5,743,941 | 4/1998 | Gerner et al. | 96/10 |

FOREIGN PATENT DOCUMENTS 376638  7/1990  European Pat. Off. ............ 96/6

*Primary Examiner*—C. Scott Bushey
*Attorney, Agent, or Firm*—Orrin M. Haugen, Esq.

[57] ABSTRACT

A vacuum degassing and solvent delivery apparatus for those solvents being utilized in high pressure liquid chromatographic operations and/or applications. The degassing and delivery apparatus of the present invention is designed for attachment directly to a solvent reservoir, such as a double-ended bottle having a threaded portion along the bottom end thereof. The arrangement facilitates ease of installation and removal of the vacuum degassing, recycling and delivery apparatus so as to accommodate a variety of installation applications and requirements. The solvent degassing system of the present invention further includes the utilization of an atmospheric impermeable composite tubing structure which is effective for isolating fluids from atmospheric contamination during transport.

6 Claims, 2 Drawing Sheets

TO HPLC PUMP

SOLVENT RECEPTACLE AND DEGASSER FOR USE IN HIGH PRESSURE LIQUID CHROMATOGRAPHY

CROSS-REFERENCE TO RELATED APPLICATION

The present application is a continuation-in-part of continuation-in-part application Ser. No. 08/688,439, filed Jul. 30, 1996 and entitled "BOTTLE TOP SOLVENT DEGASSER", now U.S. Pat. No. 5,743,941, which is a continuation-in-part of parent application Ser. No. 08/468,016, filed Jun. 6, 1995, and entitled "ATMOSPHERE IMPERMEABLE TUBING FOR USE IN HIGH PRESSURE LIQUID CHROMATOGRAPHY", now abandoned.

BACKGROUND OF THE INVENTION

The present invention relates generally to an improved vacuum degassing, recycling and solvent delivery apparatus for solvents utilized in high pressure liquid chromatographic operations and/or applications, and wherein the solvent degassing, recycling and delivery apparatus is adapted for removable retention on a solvent reservoir, and wherein the system is essentially self-priming. The vacuum degassing solvent treating arrangement of the present invention is particularly designed for use in those systems wherein portions of the solvent being utilized are recycled back to the original supply reservoir and where degassing is necessary for solvent use. The solvent degassing system of the present invention further includes, as a feature, the utilization of an atmospheric impermeable composite tubing structure which is effective for isolating fluids from atmospheric contamination during transport.

The present invention is an improvement over the vacuum degassing systems disclosed in U.S. Pat. No. 5,340,384 (Sims), and that system disclosed in copending application Ser. No. 08/688,439, both of which are assigned to the same assignee as the present invention. The content of U.S. Pat. No. 5,340,384 and application Ser. No. 08/688,439 are incorporated by reference herein. While the systems disclosed in the U.S. Pat. No. 5,340,384 patent and application Ser. No. 08/688,439 function well, the present arrangement provides an advantage in terms of versatility in use and also in priming of the system.

One of the analytical chemical operations which involves the use of liquid solvents in which dissolved gases, particularly air, is detrimental and undesirable is high pressure liquid chromatography (hereinafter referred to as HPLC). In HPLC applications, the presence of small quantities of dissolved gases interferes with the accuracy and indeed the total sensitivity of the system and its operation. Furthermore, if the dissolved species is chemically reactive, such as oxygen from dissolved air, the quality of the liquid solvent is adversely affected. As the quantity of the dissolved species increases, the adverse affect likewise increases. Thus, in order to avoid these undesirable side effects, the dissolved species are typically removed by one or more degassing operations. The overall operation, particularly the HPLC operation, is rendered far more efficient when degassing can be undertaken expeditiously and without incurring additional or significant delays. Additionally, the system of the present invention utilizes a form of atmospheric impermeable composite tubing which effectively transports the liquid solvents through the system so that the solvent is isolated from potential contaminants such as the oxygen component in ambient air.

In the past, various techniques have been employed for removal of dissolved gases from HPLC solvents. These included heating of the liquid or alternatively, subjecting the solvent liquid to a reduced pressure or vacuum. Exposure of the solvent to a source of ultrasonic energy has also been employed. Degassing involving the passing of a fine stream of an inert gas such as helium or the like through the solvent has also been utilized in the past. Helium degassing and/or sparging has certain disadvantages including the selective removal of certain volatile components of mixed solvents, and furthermore requiring the presence of large vessels for the helium supply. Membrane apparatus has been successfully employed for vacuum degassing of HPLC solvents.

In certain HPLC applications, it is desirable to employ a degassing apparatus which has been thoroughly cleaned and the presence of even trace amounts of any previously employed solvent have been eliminated. In accordance with a feature of the present invention, a quick changeover vacuum degassing device has been developed which is adapted for removable retention on a solvent reservoir, particularly a bottle having a threaded opening along its bottom or base. The degassing device includes a threaded means for engaging the base threaded opening of the reservoir or bottle, with the degassing system being conveniently confined within a shrouded zone forming a vacuum chamber for housing and retaining the degassing tubing. The inlet to the reservoir is preferably arranged and disposed in the upper end of the double-ended bottle, and for purposes of accommodating flow, a vent hole may be positioned in the cap area accommodating the inlet tube. Thus, by simply engaging the threads and screwing the attachment mechanism onto the base of the bottle, the vacuum degassing and recycling apparatus of the present invention is expeditiously placed into the system for operation. Also, the apparatus of the present invention contains means for readily receiving and coupling tubing of the type typically utilized in HPLC applications, and further includes the utilization of atmospheric impermeable composite tubing which effectively isolates the solvent, particularly solvent which has been previously degassed, from exposure to atmospheric contaminants. Additionally, an integral valve structure is conveniently incorporated into the degassing mechanism.

SUMMARY OF THE INVENTION

Briefly, in accordance with the present invention, a vacuum degassing and recycling apparatus is provided for HPLC solvents, with the apparatus comprising a body member adapted for removable retention on the base of a double-ended solvent reservoir. First coupling means are provided for attaching or otherwise coupling the degassing apparatus between the solvent reservoir and an HPLC apparatus utilizing a pump along with other components designed and utilized for performing the HPLC operation. This coupling means includes atmospheric impermeable composite tubing structure which is described in detail hereinafter. Second coupling means are provided which include a means for coupling the degassing apparatus to a solvent recycler, thereby coupling the recycler to the solvent reservoir for receipt of recycled solvent which is received from the HPLC apparatus. Additionally, a removable inlet port is formed in the cap positioned in the upper end of the double-ended bottle forming the reservoir.

The solvent reservoir includes a double-ended bottle with a bottom attachment comprising a degassing chamber in which thin-walled tubing is received, and which forms a vacuum chamber for exposure of the tubing to low pressures. A vacuum port is formed in the body for coupling to a suitable vacuum-generating source. A first solvent receiving port is formed within the body of a cap for the lower end of the double-ended bottle reservoir for delivery of solvent from a zone adjacent the base of the reservoir to the degassing tube disposed within the vacuum chamber. A second solvent delivery port is provided for delivery of the degassed solvent from the degassing tube into a fluid line for transfer to the HPLC apparatus. A solvent recycler apparatus is provided, and a port is provided in the degassing apparatus for receiving recycled solvent from the recycler apparatus for direct delivery into the reservoir.

In use, the vacuum degassing apparatus of the present invention is well adapted to handle HPLC solvents, and for versatility in use, is adapted for ease of installation and removal on the solvent reservoir. The degassing apparatus may be cleaned and otherwise restored for subsequent use in other HPLC applications wherein the same or different solvents may be employed. Furthermore, since the solvent receiving port for accepting solvent for delivery to the degassing tube is disposed adjacent the base of the reservoir, the solvent present provides substantially continuous modest head pressure which in turn provides for the self-priming feature in the system.

Therefore, it is a primary object of the present invention to provide an improved vacuum degassing apparatus for HPLC solvents, wherein the apparatus is both arranged and adapted for ease of installation and removal directly from the double-ended solvent reservoir, and with the present invention further providing an effective means for aiding the pump for transporting HPLC solvents in an atmospheric impermeable composite tubing structure.

It is a further object of the present invention to provide an improved vacuum degassing apparatus for HPLC solvents wherein the degassing chamber is formed within a reservoir assembly, and with the chamber being provided with appropriate inlet and outlet ports for expeditious transfer of HPLC solvents to and from the reservoir, with the operation of the pump being simplified and expedited by virtue of a self-priming feature being made available through the configuration of the solvent delivery portion of the system.

Other and further objects of the present invention will become apparent to those skilled in the art upon a study of the following specification, appended claims, and accompanying drawings.

IN THE DRAWINGS

DESCRIPTION OF THE PREFERRED EMBODIMENT

Figure 1:
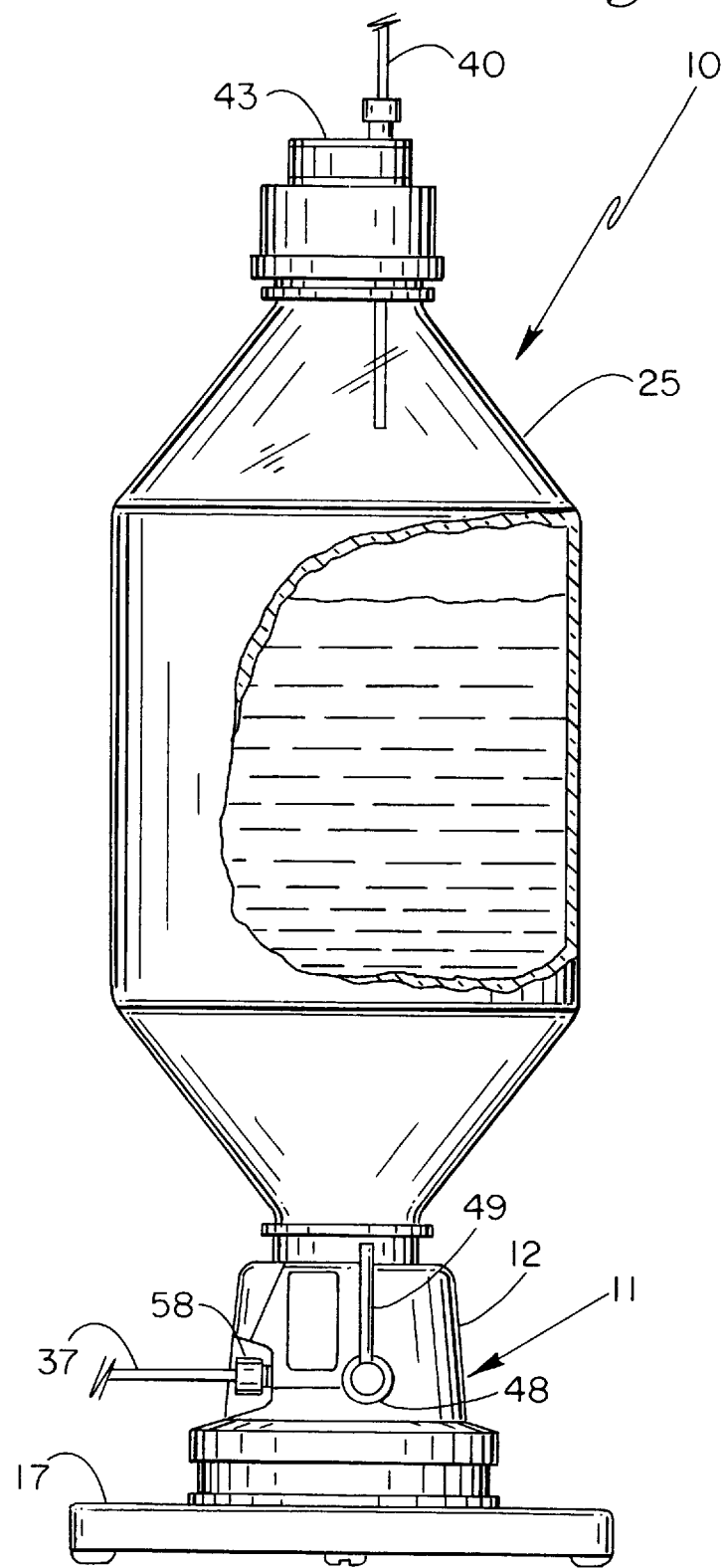
FIG. 1 is a vertical sectional view taken across the diameter of a vacuum degassing apparatus in accordance with the present invention, and with the apparatus, as shown, being coupled to the threaded base portion of a double-ended bottle reservoir, with portions of the bottle reservoir being broken away to expose the interior.
Figure 2:
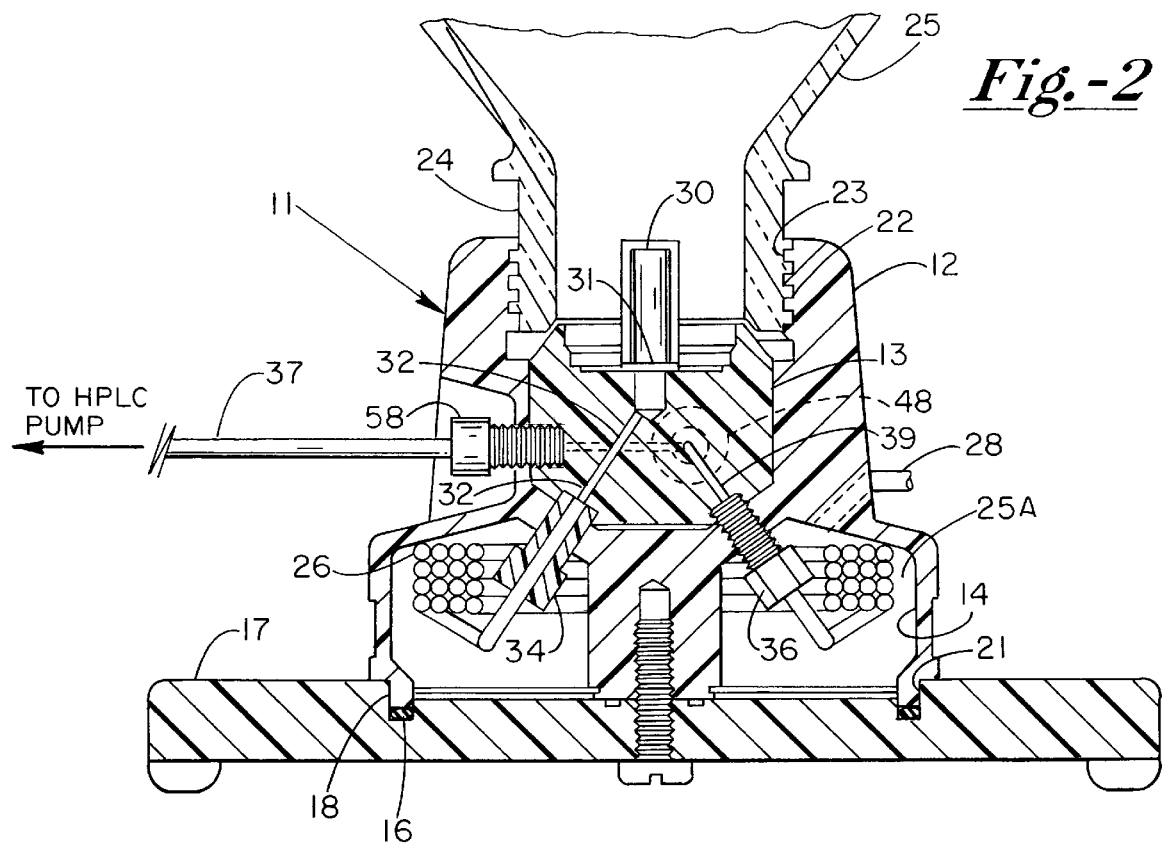
FIG. 2 is a vertical sectional view of a fragmentary portion of a solvent reservoir having the degassing apparatus of the present invention secured to the bottom thereof.
Figure 3:
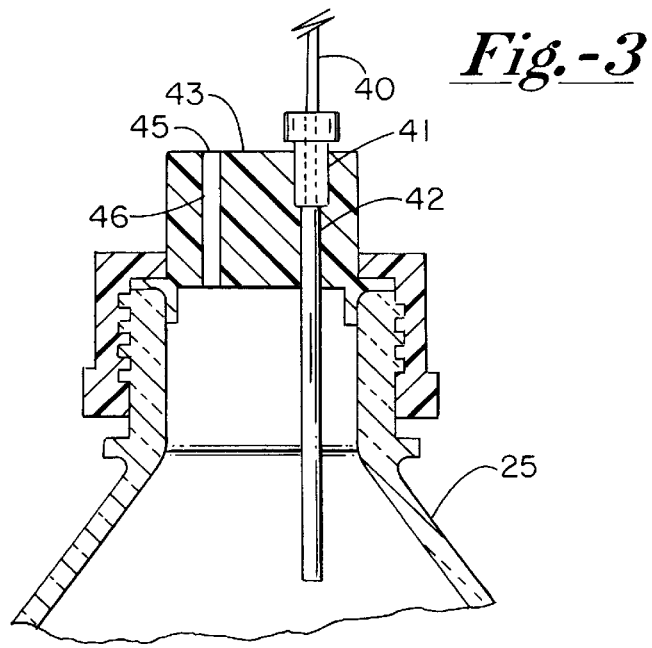
FIG. 3 is a fragmentary vertical sectional view of the cap portion of the apparatus attached to the upper end of a double-ended bottle reservoir.

In accordance with the preferred embodiment of the present invention and with particular attention being directed to FIGS. 1 and 2 of the drawings, the vacuum degassing apparatus and system generally designated 10 includes a degassing base assembly and dispenser shown generally at 11, with the base assembly having a body shroud portion 12 together with a central core 13 in the shroud, and a lower flanged portion 14 in shroud 12. Shroud 12, core 13 and flanged portion 14 are all coupled together in a gas-tight arrangement through the implementation of appropriate O-ring seals as shown at 16. Sleeve portion 18 having an inwardly extending end portion engages the bore formed in base 17 as within annular groove 21. The upper threaded feature as illustrated at 22 is designed to engage complementary threaded portions 23 disposed on the base portion 24 of solvent reservoir bottle 25. As illustrated in the drawings, reservoir bottle 25 is a double-ended bottle which is provided with a pair of opposed threaded ends. While a single-ended reservoir bottle may be employed, a double-ended reservoir bottle is generally preferred for ease of introduction of solvent into the system without creation of a vacuum, and also for facilitating cleaning for reuse.

In order to achieve gas-tight relationship between core 13 and shroud 12, a relatively hard plastic material is utilized for fabrication of shroud 12. A preferred material when plastic resin materials are employed being for core 13 is a polymer of polytetrafluoroethylene available under the trade designation "Teflon" from E. I. DuPont de Nemours & Co. of Wilmington, Del. Core 13 is pressed into shroud 12 using an over-press to form a seal. For a material of construction for the mating portion of shroud 12, high density polypropylene polymer is preferred.

As has been indicated, shroud 12, core 13, together with flange member 14 provide an enclosure or vacuum chamber as at 25A for the degassing coil such as shown at 26. The details of the degassing coil are provided in U.S. Pat. No. 5,340,384 referred to hereinabove. A vacuum port is provided for communication between chamber 25A and a source of vacuum, with the vacuum port bore being shown at 28. A suitable fitting for receiving the vacuum line is provided but not illustrated.

Degassing coil 26 is in communication with the interior of reservoir 25 by means of filter element 30, with filter element 30 being engaged or coupled to core 13 through tubing coupling 31. Coupling 31 is, of course, suitably engaged in core 13 to provide communication between bore 32 and filter element 30. Fitting 34 provides a means to couple bore 32 with the interior of coil 26. The fitting shown at 36 provides communication between the downstream end of coil 26 and outlet tubing 37. Fitting 38 is utilized to couple outlet bore 39 with outlet tubing 37 in a manner similar to that illustrated or discussed hereinabove. Outlet tube 37 is also known as a pick-up or delivery line. In order to effectively isolate and protect the solvent being transferred within tubing 37, this tubing is preferably an atmospheric impermeable composite tubing structure which is effective to isolate the fluids from atmospheric contamination during transport. The tubing comprises concentrically arranged co-extruded inner and outer tubular components, all of which is described in detail in copending application Ser. No. 08/688,439, filed Jul. 30, 1996 and entitled "BOTTLE TOP SOLVENT DEGASSER" and Ser. No. 08/468,016, filed Jun. 6, 1995 and entitled "ATMOSPHERE IMPERMEABLE TUBING FOR USE IN HIGH PRESSURE LIQUID CHROMATOGRAPHY", now abandoned.

In order to provide a recycling feature for this apparatus, return or recycle line 40 is coupled to fitting 41, and thereby placed in communication with bore 42 in cap 43 which delivers recycled fluid into reservoir 25 as a receptacle for recycled or returned solvent. A vent hole or Luer accommodating port is provided as at 45, with this port communicating, in turn, with the interior of reservoir 25 through bore 46. This vent hole may be employed to provide a vent to atmosphere, or alternatively to accept or receive a Luer fitting to accommodate a syringe or other device which may either increase or reduce the pressure within the confines of the solvent reservoir or accept a filter element to prevent contaminants from entering the head space of the pump.

With continued attention being directed to the drawings, reservoir 25 having vacuum degassing and solvent delivery apparatus 11 is coupled to the base of reservoir 25. Degassing and solvent delivery apparatus 11 is provided with an outlet or delivery line 37 which delivers degassed solvent to a pump not shown, which transfers the solvent under pressure to the HPLC apparatus. HPLC apparatus are well known in the art and are well recognized and understood by those of conventional skill in the art. A line delivers spent or recyclable solvent from the HPLC apparatus into a solvent recycler system or apparatus, with recycler apparatus also being well known in the art. Spent or waste solvent is disposed of through a waste line, with a return line 40 delivering recycled or restored solvent for return to solvent reservoir 25. The details of such a system are, of course, illustrated in copending application Ser. No. 08/688,439 referred to hereinabove.

In order to simplify the system without compromising the integrity thereof, an integral valve such as valve 48 is provided integrally within the degassing assembly. The presence of valve 48 with its actuating lever or handle 49 assists in control of fluid flow from solvent reservoir 25 through the balance of the system.

The atmospheric impermeable tubing 37 preferably comprises a pair of concentrically arranged co-extruded tubular components, with the inner tubular component being fabricated of a fluorinated polymer selected from perfluoroalkoxy ethylene (Teflon PFA) or fluorinated ethylene propylene (Teflon FEP), and with the outer tubular component consisting essentially of polyvinylidine fluoride. Polyvinylidine fluoride is frequently designated PVDF in the industry. Both inner and outer tubular components are formed of simultaneously and co-extruded resins, and when cooled, are formed along a common central axis.

Typical tubing utilization includes polytetrafluoroethylene (Teflon) along with certain other materials. The use of such tubing however has been found to suffer from mechanical, optical and/or chemical problems which are not solved through the use of a single wall tubing. The composite co-extruded structure described herein has been found to possess unusual and exceptional properties for isolating the fluids from atmosphere. The utilization of such tubing has been found to permit and accommodate the utilization of a solvent reservoir which may provide modest head pressure to the system over extended periods of time.

With attention being directed to FIG. 2, tubing 37 is an atmospheric impermeable composite tubing structure particularly adapted for isolating fluids from atmospheric contamination. In its formation, the composite tubing is formed through simultaneous extrusion or co-extrusion of the individual components along a common axis. When appropriately formed along a common axis, the outer surface of the inner tubular component is in substantially full contact with the inner surface of the outer tubular component so as to enhance the overall atmospheric isolation properties of the composite structure. As indicated, since the individual components are substantially incompatible, one with another, and being immiscible, the finished product comprises the composite arrangement which is mechanically bonded or held together. In other words, the immiscibility of the liquid resins precludes the chemical bonding of the tubular components along their mutually adjacent surfaces. The details of the preparation of such tubing is set forth in application Ser. No. 08/468,016 as well as in copending application Ser. No. 08/688,439.

Fluorinated ethylene-propylene resins typically comprise a copolymer of tetrafluoroethylene with hexafluoropropylene. Such material is perfluoroalkoxy ethylene, typically designated "Teflon PFA". All such materials are commercially available, with Teflon PFA being available from E.I. DuPont deNemours & Co. Of Wilmington, Del. This copolymer provides a resultant product with properties generally similar to Teflon (polytetrafluoroethylene). This material has a somewhat higher coefficient of friction as compared to polytetrafluoroethylene which renders it desirable for this intended application. Fluorinated ethylene-propylene resin is available commercially as an extrusion powder.

Polyvinylidine fluoride is a fluorocarbon polymer which is resistant to degradation from contact with oxygen. Polyvinylidine fluoride is also recognized as being resistant to attack by acids, alkalis, halogens, and the like. These materials are, of course, readily commercially available.

In the preparation of the product, the extruder is normally employed and configured in such a way that the inner tubular component is formed initially, and cooled to a point where it becomes reasonably durable and with its wall thickness resistant to collapse. At that time, the outer tubular component is applied and the entire tubular assembly permitted to cool down. These techniques are well known in the art and achieved and accomplished without the requirement of substantial experimentation. Other techniques may, of course, be utilized and/or incorporated in the preparation of the product, including the incorporation of the inner tubular component within a previously-formed outer tubular component.

In connection with the apparatus of the present invention, HPLC applications may be undertaken with solvents appropriately degassed and recycled, and wherein the solvent reservoir bottle employed as a dispenser may be readily attached and detached from the system to provide and facilitate cleaning and restoration of the degassing and solvent delivery apparatus for use on subsequent operations and applications.

It will be understood that the apparatus illustrated herein is for purposes of illustration only and those of ordinary skill in the art may depart from the examples and specific illustrations herein without actually departing from the spirit and scope of the present invention.

What is claimed is:

1. Vacuum degassing and solvent delivery apparatus for handling HPLC solvents and adapted for removable retention on a solvent reservoir and having coupling means for coupling of the degassing apparatus between said solvent reservoir and an apparatus having a pump and arranged to perform an HPLC operation, said vacuum degassing apparatus comprising:

(a) a solvent reservoir having a retention means secured to the base thereof for removably coupling and receiving a solvent degassing and solvent delivery assembly thereon, said degassing and delivery assembly including a closed body with a coiled degassing tube disposed in a vacuum chamber formed within said closed body, and with a vacuum port being formed in said body and being in communication with said vacuum chamber;

(b) a first solvent receiving port formed within said body for delivery of solvent from the base of said reservoir to said coiled degassing tube;

(c) a solvent delivery port for delivery of degassed solvent from said coiled degassing tube to a fluid line, said fluid line being in communication with an HPLC pump for transferring degassed solvent from the base of said reservoir under the static pressure of solvent retained in said solvent reservoir to said HPLC pump.

2. The degassing and solvent delivery apparatus of claim 1 being particularly characterized in that said removable retention means comprises a threaded end for coupling in fluid tight relationship to said solvent reservoir.

3. The degassing and solvent delivery apparatus of claim 2 being further characterized in that said coiled degassing tube extends continuously from said first solvent receiving port to said solvent delivery port.

4. The degassing and solvent delivery apparatus as defined in claim 1 being particularly characterized in that the degassing assembly has complementary removable retention means for mating with the retention means formed on the base of said reservoir and arranged for isolating the contents of said reservoir from the ambient.

5. The degassing and solvent delivery apparatus as defined in claim 1 being particularly characterized in that said reservoir is a double-ended bottle having threaded openings at opposed ends thereof.

6. The degassing and solvent delivery apparatus as defined in claim 4 being particularly characterized in that a valve is provided within said degassing assembly to control flow of fluid from said solvent reservoir.

* * * * *